US00PP20167P2

(12) United States Plant Patent
Durand

(10) Patent No.: US PP20,167 P2
(45) Date of Patent: Jul. 7, 2009

(54) CRABAPPLE TREE NAMED 'DURLEO'

(50) Latin Name: *Malus adstringens*
Varietal Denomination: Durleo

(75) Inventor: James Richard Durand, Portage la Prairie (CA)

(73) Assignee: Durand & Graham Ltd., Portage La Prairie, Manitoba (CA)

( * ) Notice: Subject to any disclaimer, the term of this patent is extended or adjusted under 35 U.S.C. 154(b) by 0 days.

(21) Appl. No.: 12/082,747

(22) Filed: Apr. 14, 2008

(51) Int. Cl.
*A01H 5/00* (2006.01)

(52) U.S. Cl. ..... Plt./173
(58) Field of Classification Search ..... Plt./173
See application file for complete search history.

*Primary Examiner*—June Hwu
(74) *Attorney, Agent, or Firm*—Penny J. Aguirre

(57) ABSTRACT

A new and distinctive cultivar of flowering crabapple, botanically known as *Malus* 'Durleo' is characterized by a uniquely compact upright crown form, superior winter hardiness in northern zones, glossy bronze-purple leaves, an abundance of medium pink flowers, small ornamental fruit and high disease resistant 'Durleo' has an unusual characteristic of creating bole-like bumps on its bark once it attains a trunk diameter of over 2 inches caliper. The new cultivar is particularly suited for use as an accent ornamental flowering tree, attractive in a group landscape planting and planted in a row for a screen.

3 Drawing Sheets

Botanical classification: *Malus×adstringens*.
Variety denomination: 'Durleo'.

BACKGROUND OF THE INVENTION

The present invention relates to a new and distinct cultivar of *Malus* of hybrid origin and will be referred to hereafter by its cultivar name, 'Durleo'. 'Durleo' is a deciduous tree grown for use as an ornamental landscape plant.

The inventor collected seeds in winter of 1990 from a single unnamed, extremely hardy *Malus* tree growing in a neighbor's garden in Portage 1a Prairie, Manitoba, Canada. The parent plant was planted in the early 1970s in a group of seedlings derived from open pollination of 'Royalty' (not patented). Many of the seedlings had been removed by 1990 due to disease. The inventor collected seeds from the surviving tree that showed the best resistance to fireblight and fungal apple scab. The resulting seedlings were grown and evaluated by the inventor at his nursery and the new cultivar, 'Durleo', was selected in 1992 as a single unique plant.

Asexual reproduction of the new cultivar was first accomplished by budding of budwood on *Malus* rootstock by the inventor in 1992 in Portage 1a Prairie, Manitoba, Canada The new cultivar has also been propagated under different environments in other areas of Canada and the characteristics of this cultivar have been determined to be stable and are reproduced true to type in successive generations.

SUMMARY OF THE INVENTION

The following traits have been repeatedly observed and represent the characteristics of the new cultivar as observed for the original tree (17 years in age) as grown at Portage 1a Prairie, Manitoba, Canada, as well as upon the study of its asexually budded progeny. These attributes in combination distinguish 'Durleo' as a unique cultivar of *Malus*.

1. 'Durleo' exhibits an upright oval crown form that is not commonly observed in crabapples, which is useful for planting in areas where a reduced crown spread is desired and for use as a hedge for screening.
2. 'Durleo' exhibits improved hardiness for northern zones with a hardiness in U.S.D.A. Zone 3 with a high degree of tolerance to winter sunscald damage to the trunk and with no evidence of winter damage observed to the branch tips for which *Malus* cultivars in U.S.D.A. Zone 4 and colder are typically susceptible.
3. 'Durleo' exhibits good resistance to apple scab and a high level of resistance to fireblight.
4. 'Durleo' exhibits small bole-like structures that develops on the bole once the tree reaches the 2 inch caliper stage and larger.
5. 'Durleo' exhibits consistent foliage that is glossy and turns bronze purple color during the growing season.
6. 'Durleo' has moderate to high production of fragrant flowers followed by small fruit that is persistent until early winter.

The new cultivar can be compared to 'Royalty', 'Pink Spires' (not patented), and 'Thunderchild' (not patented). 'Durleo' is similar to 'Royalty' in having glossy leaves, an upright compact form and dark purple fruit, however 'Royalty' differs from 'Durleo' in having a more rounded form, and in having a severe susceptibility to fireblight and apple scab, and in having less flowers that are produced a week later in the season. 'Durleo' is similar to 'Thunderchild' in growth rate, blooming time, compact upright form and resistance to fireblight, however, 'Thunderchild' differs from 'Durleo', however in having a broader crown, in having susceptibility to apple scab, leaves that are not as glossy, and fruit that is retained for a month less. 'Durleo' is similar to 'Pink Spires' in having an upright crown form, however, 'Pink Spires' differs from 'Durleo' in having a different leaf color, less resistance to fireblight and apple scab and in having more persistent fruit.

BRIEF DESCRIPTION OF THE DRAWING

The accompanying colored photographs illustrate the overall appearance and distinct characteristics of the new

*Malus* as grown in Portage 1a Prairie, Manitoba, Canada and. The plants in the photograph are about 5 years in age with 'Durleo' budded onto *Malus* rootstock. The colors in the photographs are as close as possible with the digital photography techniques available, the color values cited in the detailed botanical description accurately describe the colors of the new *Malus*.

DETAILED BOTANICAL DESCRIPTION

Figure 1:
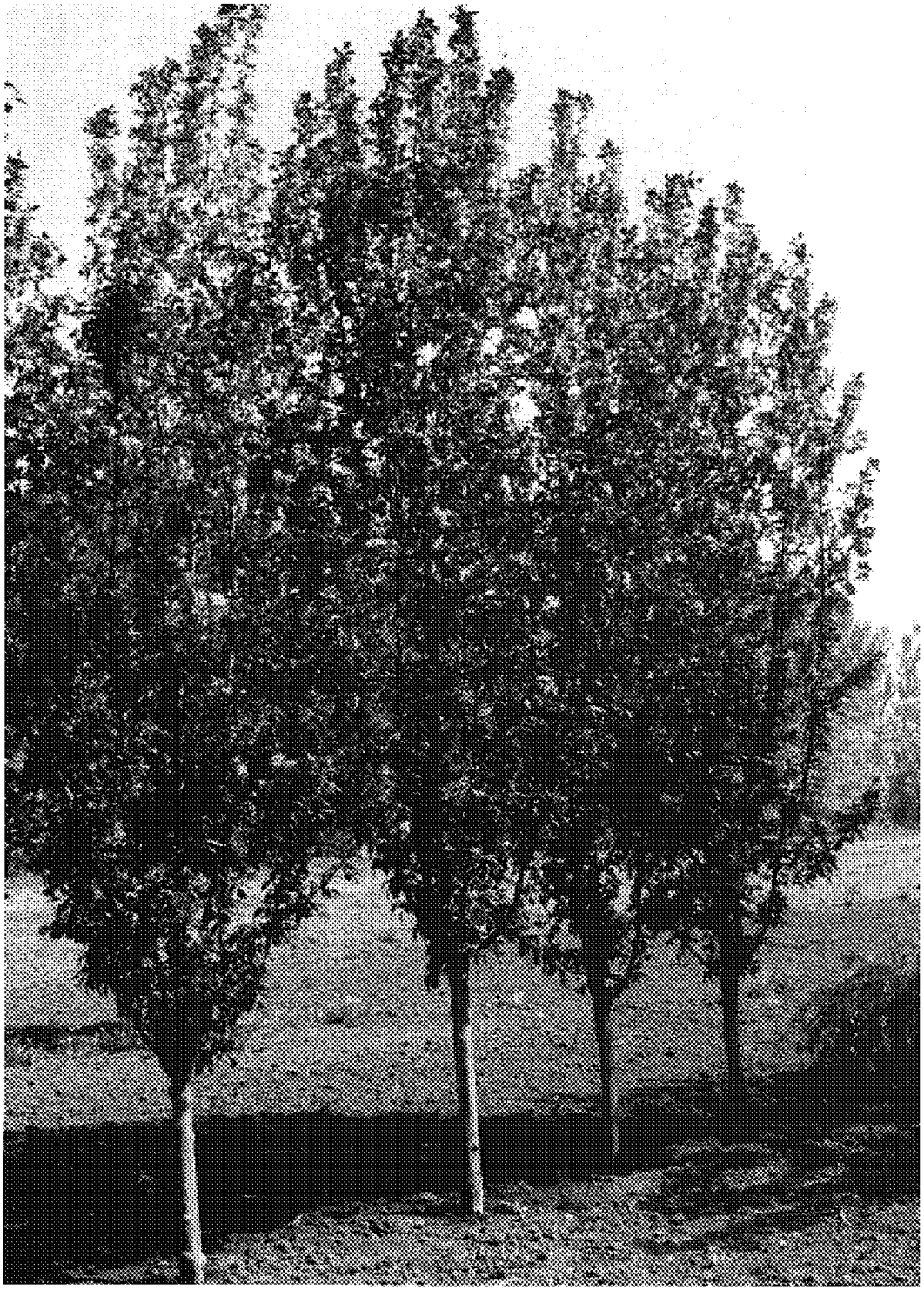
FIG. 1 is a side view of a row of plants in spring and illustrates its high production of flowers and upright habit.
Figure 2:
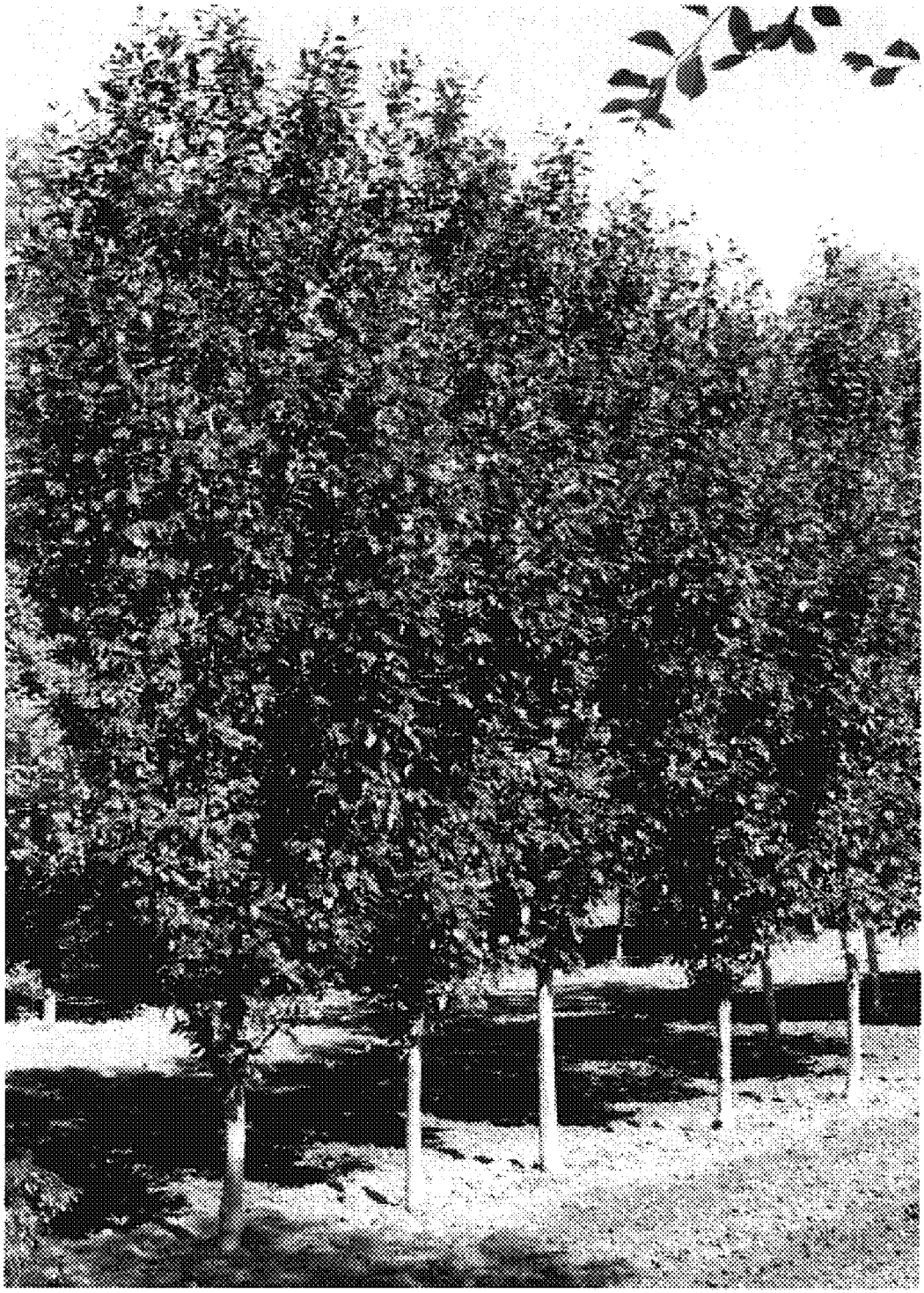
FIG. 2 is a side view of a row of plants in late summer and illustrates its glossy bronze foliage and upright habit.
Figure 3:
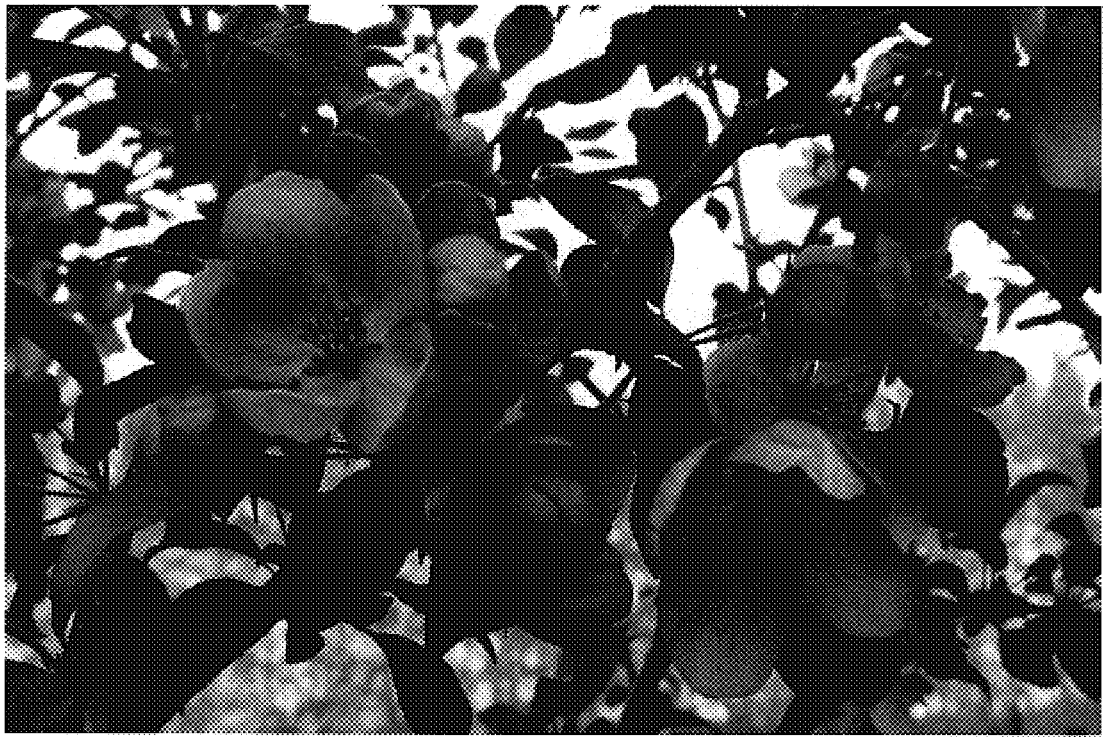
FIG. 3 provides a close-up view of the flowers.
Figure 4:
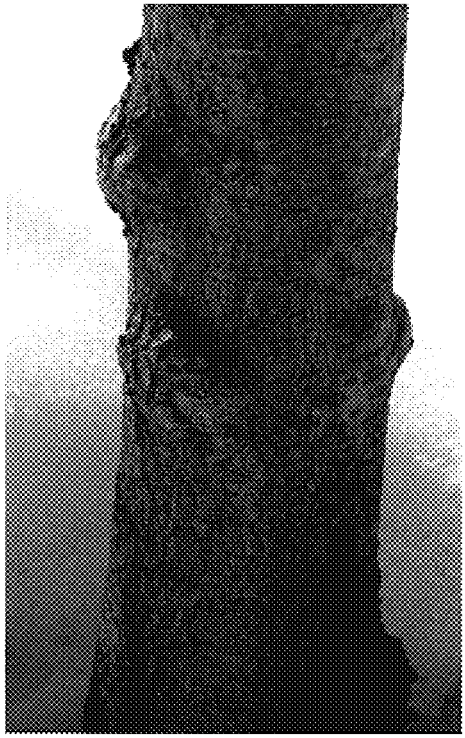
FIG. 4 provides a close-up view of the bole-like structures that develop on a tree after reaching a caliper of 2 inches or greater.
Figure 5:
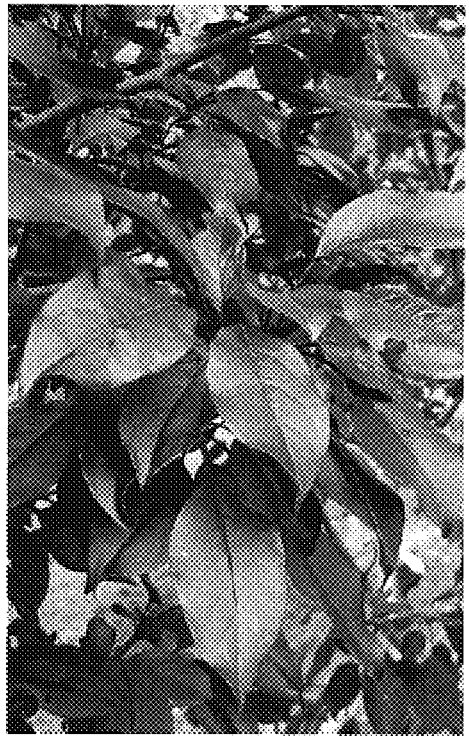
FIG. 5 provides a close-up view of the foliage.

The following is a detailed description of the new cultivar as observed for the original tree of 'Durleo' (17 years in age) and of 4 year-old plants 'Durleo' budded onto *Malus* rootstock in Portage 1a Prairie, Manitoba, Canada. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Tree description:

*Tree habit.*—Compact upright oval-shaped crown.

*Height and spread.*—A four-year old budded plant reached an average of 3.5 m (11.6 ft), the original plant reached about 7.9 m (26 ft) and 2.54 m (10 ft) in width.

*Diseases and pests.*—Superior resistance has been shown to fireblight and apple scab, virus testing is still in progress with no viruses found to date.

*Cold hardiness.*—U.S.D.A. Zone 3.

*Branching habit.*—Sharp angled branches with lateral branches held at an angle of about 35° to the main stem.

*Propagation.*—Budding onto *Malus* root stock.

*Time required for graft development.*—About 4 weeks to develop in a 36-cell tree pot.

*Growth rate.*—Moderate, grows about 40.4 cm (15.9 inches) per year.

*Trunk.*—About 5 cm (2 inches) in width in four years (measured at 30 cm from base of tree), bark is 199B in color overlaid with 202 with prominent lenticels and bole-like structures that develop once trunk is 2 inches (5 cm) in caliper.

Description of dormant shoots (one year old):

*Pubescence on upper side.*—Medium.

*Shine of bark.*—Weak

*Thickness of shoot at center of middle internode.*—Average of 2 mm.

*Bark color.*—Reddish brown 183B.

*Shoot angle.*—Approximately 45°.

*Lenticels.*—About 22 per 5 square cm of trunk, 202D to N200 in color and an average of 5 mm in length and 1.5 mm width.

Description of new growth:

*Color.*—A blend of 79A and 200A.

*Pubescence.*—None.

*Lenticels.*—About 18 per 5 square mm of new branch growth, 36A in color and an average of 1 mm in length and 0.5 mm in width.

Leaf description:

*Leaf orientation.*—Outward.

*Leaf division.*—Simple.

*Leaf shape.*—Elliptic.

*Leaf size.*—Average of 8.5 cm in length and 4.3 cm in width ($4^{th}$ to $6^{th}$ leaf).

*Leaf apex.*—Acute to cuspidate.

*Leaf base.*—Cuneate.

*Leaf surface.*—Glossy on upper surface and lower surface.

*Leaf margin.*—Finely serrated.

*Leaf color.*—Spring upper surface; 143B, spring lower surface; 143B, late summer upper surface; blend of 79A and 147A, late summer lower surface; blend of 137C and 194A, fall color upper surface; blend of 79A and 187A, fall color lower surface; blend of 187A and 194A.

*Leaf venation.*—Pinnate main veins with netted minor veins, color matched leaf color.

*Petioles.*—Average of 2.7 cm in length and 2 mm in diameter, glossy surface, 79A in color.

*Stipules.*—79A in color, an average of 1 cm in length and 2 mm in width, glossy surface.

Flower description:

*Flowering period.*—Early to mid season.

*Beginning flowering date.*—Typically about May $10^{th}$ in Manitoba.

*Number of flowers.*—Average of 5 per cluster and 65 per branch that is 100 cm in length.

*Inflorescence type.*Corymb of rotate flowers.

*Flower buds.*—59B to 59D in color prior to opening, round in shape, average of 2 cm in length and 5 cm in diameter.

*Flower size.*—Average of 3.5 cm in diameter and 2 cm in depth.

*Flower fragrance.*—Mild.

*Flower aspect.*—Outward.

*Petals.*—5 per flower, un-fused, partially overlapping, ovate to obovate in shape, obtuse apex, round base, entire margin, about 1.7 cm in length and 1.2 cm in width, color of upper surface and lower surface is a blend of 64B, 69D and 75C, upper and lower surface is smooth and semi-glossy.

*Sepals.*—5 per flower, 60A in color with tips 60B (upper and lower surface), slight to moderate pubescence, triangular in shape, entire margin, acute apex, fused base, average of 0.5 cm in length and 1 mm in width, surface is moderately pubescent

*Pedicel.*—184A in color, average of 2.5 cm in length and 1 mm in width, surface is Lightly pubescent.

*Pistil.*—Compound carpel with 3 stigmas fused at base, 1.2 cm in length, style is 60A in color and 7 mm in length, stigma is 160A in color, ovary is pubescent and 160A in color.

*Stamens.*—About 20 per flower, anther is oblong in shape, 59A in color and 1.5 mm in length, pollen is 4A in color and moderate in quantity.

Fruit description:

*Shape.*—Round.

*Size.*—Average of 1 cm in diameter.

*Skin.*—Smooth surface and color is 59A when mature and dries to 177A.

*Flesh.*—Texture and color.

*Stalk.*—Size and color and depth and width of stalk cavity.

*Seed.*—Nearly renal-shaped, 3 per fruit, about 5 m in length and 2.5 mm in width, 177A in color.

It is claimed:

1. A new and distinct cultivar of crabapple tree named 'Durleo' as herein illustrated and described.

* * * * *